United States Patent [19]

Levinson et al.

[11] 4,056,102
[45] Nov. 1, 1977

[54] SPRING ACTUATED MEDICAL INJECTOR

[76] Inventors: Melvin Levinson, 7330 SW. 62nd Place, Miami, Fla. 33143; Goodwin Salkoff, 450 Tivoli, Coral Gables, Fla. 33134

[21] Appl. No.: 717,355

[22] Filed: Aug. 24, 1976

[51] Int. Cl.² ............................................. A61M 5/00
[52] U.S. Cl. .................................................. 128/218 F
[58] Field of Search ................... 128/215, 216, 218 R, 128/218 F, 234

[56] References Cited
U.S. PATENT DOCUMENTS 2,295,849  9/1942  Kayden .............................. 128/218 F

FOREIGN PATENT DOCUMENTS 452,341  4/1950  Italy .................................. 128/218 F Primary Examiner—John D. Yasko
Attorney, Agent, or Firm—Salvatore G. Militana

[57] ABSTRACT

A spring actuated medical injector for the continuous injection of dye, medication, etc. into a patient having a handle, a syringe holder, an actuating arm extending from a coil spring to the position of the syringe holder all made of a single length of wire and a detent plate member pivotally mounted on the handle for restraining and releasing the actuating arm whereby the actuating arm resting on the plunger of the syringe will exert a continuous force thereon until the fluid in the syringe has been expelled.

6 Claims, 5 Drawing Figures

U.S. Patent  Nov. 1, 1977  4,056,102
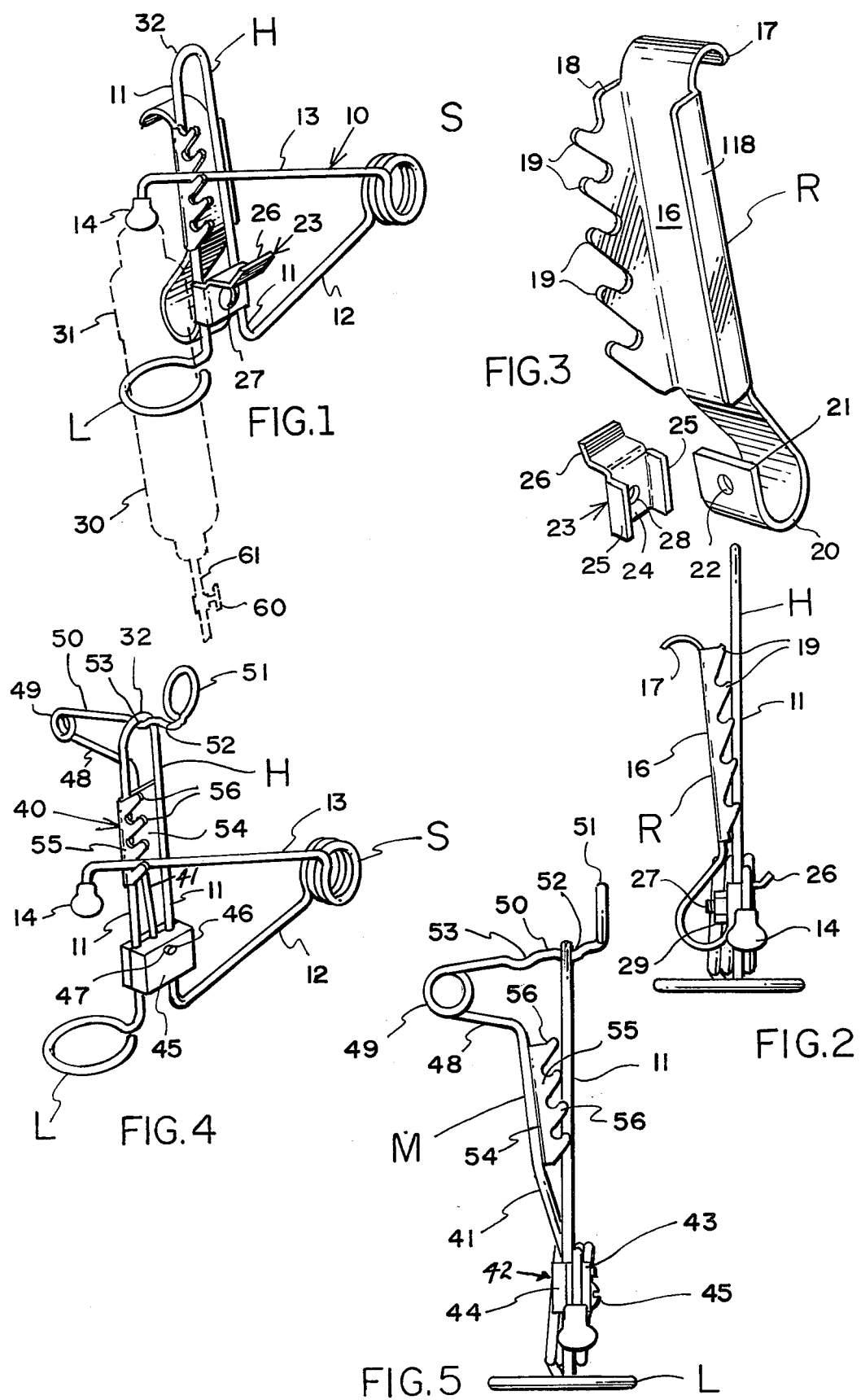

4,056,102

SPRING ACTUATED MEDICAL INJECTOR

BACKGROUND OF THE INVENTION

1. Field of the Invention

This invention relates to injection devices and is more particularly directed to a medical injector that is actuated by a coil spring.

2. Description of the Prior Art

At the present time, when a doctor wishes to inject a radiopaque fluid into the vascular system of a patient, and simultaneously therewith observe the results on an x-ray machine, the doctor must operate the syringe as he observes the x-ray or have a second person inject the fluid as he observes the x-ray. The person operating the syringe exposes himself to radiation. Conventional automatic injectors that are available are large in size, expensive in cost and difficult to maintain in a sterile condition. The present invention contemplates avoiding the above listed objections to the conventional injectors.

SUMMARY OF THE INVENTION

Therefore a principal object of the present invention is to provide a simple, inexpensive and automatically operated medical injector that does not require the exposure of an operator thereof to radiation during its use.

Another object of the present invention is to provide a small automatically operated medical injector that is readily maintained in a sterile condition, since it is sufficiently small to be received in the conventional doctor's instrument sterilizer.

A further object of the present invention is to provide a coil spring actuated medical injector that is constructed mainly of a single length of wire.

With these and other objects in view, the invention will be best understood from a consideration of the following detailed description taken in connection with the accompanying drawing forming a part of this specification, with the understanding, however, that the invention is not confined to any strict conformity with the showing of the drawing but may be changed or modified so long as such changes or modifications mark no material departure from the salient features of the invention as expressed in the appended claims.

BRIEF DESCRIPTION OF THE DRAWING

In The Drawing:

FIG. 1 is a perspective view of our spring actuated medical injector showing a syringe positioned thereon in dotted lines.

FIG. 2 is a side elevational view thereof and the syringe not shown.

FIG. 3 is a perspective view of the release member shown removed from the injector.

FIG. 4 is side elevational view of an alternate construction of our spring actuated medical injector.

FIG. 5 is a front elevational view thereof.

DESCRIPTION OF THE PREFERRED EMBODIMENTS

Referring to the drawing wherein like numerals are used to describe similar parts throughout the various figures, the numeral 10 refers to our spring actuated medical injector, the syringe 20 in position on the injector is shown by dotted lines. The frame of the injector 10 is constructed from a single length of wire shaped to form a handle H, a coil spring S and a loop shaped support L for a syringe 30. The handle H which is elongated and formed by legs 11 in parallel and spaced relation to each other joined at the top by an arcuate portion 32 support for a spring release member R. The loop shaped support L is positioned at the foot portion of one of the legs 11 while the coil spring S which is in coplanar relation with the support L is joined by a wire 12 to the foot portion of the other leg 11. An actuating wire member 13 extends from the other side of the coil spring S to the position of the loop shaped support L where a pliable tip member 14 is mounted. The tip member 14 engages the plunger 31 of the syringe 30 transferring the constant force of the coil spring S to force the plunger 31 to slide inwardly of the syringe 30.

Mounted on the handle H is the spring release member R consisting of an elongated flat wall portion 16 having an arcuate top end portion 17 for engagement by the operator's finger for actuating the release member R. Flanges 18 and 118 extend along the sides of the body member 16 engaging the leg portions 11. The flange 18 is provided with a plurality of outwardly extending finger portions 19 forming detents for receiving and retaining the actuating member 13 in its non-actuating position. The lower end of the body member 16 is bent as at 20 whereby the end portion 21 extends upwardly and is provided with an opening 22 for fastening to a stop member 23. The latter consists of a body portion 24 having side wall flanges 25 that engage the leg portions 11 and a stop plate member 26 extending outwardly of the body portion 24 for receiving the actuating member 13 after it has brought the plunger 31 to its innermost position in the syringe 30. The stop member 23 is fastened to the leg portions 11 by means of a bolt 27 that extends through an opening 28 formed in body portion 24 and opening 22 in the release member. A nut 29 threadedly mounted on the bolt 27 secures the release member R and the stop member 23 to the handle member H. The bent portion 20 is so formed that the normal position taken by the release member R with relation to the handle member H is as shown by FIG. 2 rearward of the leg portions 11 with the detents 19 rearward of and out of the path of movement of the actuating member 13. With the release member R in the position shown by FIG. 2, the actuating member 13, if in the tensioned and operating position will swing downwardly freely along the legs 11 until it comes to rest on the stop plate 26.

When it is desired to use our injector 10 for injecting a medicine into a person, the syringe 30 containing the medication is placed in the loop L and the actuating arm 13 is swung upwardly until the tip member 14 can be positioned on the plunger 31. At the same time, the release member R is swung inwardly to engage the upper end of the leg portions 11 and the actuating arm 13 is seated on one of the detents 19. The presence of the actuating arm 13 in the detent 19 prevents the outward swinging movement of the release member R.

When the time for injecting the medication contained in the syringe 30 occurs, all that need be done is swing the upper end of the release member R away from leg portions 11 as shown by FIG. 2 and the actuating arm 13 will now be released and will swing downwardly by virtue of the force of the coil spring S. The plunger 31 of the syringe 30 will slide downwardly at an even rate to provide a smooth and even discharge of the medication from the syringe 30 and into the vein of the person being injected. While the injection of the medication is taking place, the doctor is free to observe x-rays, etc. of the patient.

An alternate construction of our injector is shown by FIGS. 4 and 5, which injector 40 is identical in construction as to the wire structure of the loop L, spring S and the handle portion H. The only difference in our injectors 10 and 40 is in the construction of the release members R and M. The release member M consists of a wire member 41 that extends from a support bracket 42 made of two plates 43 and 44 mounted on either side of the leg portions 11 and secured together by a screw bolt 45. The lower end 46 of the spring wire which extends between the bracket plates 43 and 44 is bent and received in an opening 47 of the bracket plate 43 to secure the end of the release wire 41. The latter extends upwardly toward the top portion of the injector 40 where it is bent to a horizontal portion 48 that extends to a few loops forming a coil spring 49. Wire 50 connects the other side of the coil spring 49 and extends to a vertical loop 51 that is engaged by a person's finger for actuating the injector 40. Along the length of the wire 50 are two depressed portions 52 and 53 that are selectively engaged by the top portion 32 of legs 11. Welded or otherwise secured to the release wire member 41 is a release plate 54 having a flange 55 along one side with a plurality of outwardly extending detents 56, spaced from each other.

The operation of the injector 40, is identical to that described above in connection with the injector 10. In this injector, a person pulls on the loop 51 to cause the release member wire 41 to pivot about the bracket 42 and the plate 54. At this position, the recess or depressed portion 53 of the wire 50 will engage the arcuate member 32 and lock the release member M against movement. At this position, the detents 56 will extend beyond the plane of the legs 11 and can receive the actuating arm 13 as it is swung upwardly to its cocked position. Just as in injector 10, after the syringe 30 having medication therein and the plunger 31 in its extended position is placed in the loop L, the actuating arm 13 is swung to the nearest detent 56 with the top member 14 resting on the plunger 31. Upon pushing against the finger loop 51, the release member M will pivot about the bracket 42. The depressed portion 53 will be disengaged from the arcuate member 32, the detents 56 will swing rearwardly of the plane of the legs 11 until the recess 52 is engaged by the arcuate member 32. The actuating arm 13 released by the detent 56 in which it was previously resting and under the force of the coil spring S will slide downwardly along the legs 11 to compel the plunger 31 of the syringe 30 to force the medicine out of the syringe 30 and into the vein of a person in the same manner as described in connection with the injector 10.

In the operation of the injectors 10, 40 the rate of flow of fluid from the syringe 30 can be controlled by means of a stop cock 60 mounted on the tubing 61 of the syringe 30.

What I claim as new and desire to secure by Letters Patent of the United States is:

1. A spring actuated medical injector comprising a substantially elongated wire body portion, syringe holding means mounted on one end of said elongated wire body portion and extending in one direction therefrom, spring holding means formed of wire mounted on said one end of said elongated body portion and extending in a substantially opposite direction, spring means mounted on said last named means, an actuating wire arm extending from said spring means in the direction of said elongated body portion, detent means mounted on said elongated wire body portion for engaging said actuating arm and preventing the swinging movement of said actuating arm and means releasing said actuating wire arm from said detent.

2. The structure as recited by claim 1 taken in combination with substantially pliable tip means mounted on the free end of said actuating wire arm adapted to engage a plunger of said syringe.

3. The structure as recited by claim 2 wherein said elongated wire body portion, said syringe holding means, said spring holding means, said spring means and said actuating wire arm are formed and constructed from a length of wire.

4. The structure as recited by claim 3 wherein said elongated wire body portion having leg portions extending in substantially parallel and spaced relation to each other being joined at one end, said syringe holding means having a loop portion joined to the free end of one of said leg portions, said wire spring holding means extending rom the free end of the other of said leg portions, said spring means mounted on the free end of said wire spring holding means and said actuating wire arm extending from said spring means in the direction of said elongated body portion.

5. The structure as recited by claim 4 taken in combination with detent means pivotally mounted on said elongated wire body portion and engaging said actuating arm.

6. The structure as recited by claim 5 wherein said detent means comprising an elongated member extending along said wire body portion, means pivotally mounting said elongated member to said leg portions of said body portion, a substantially vertical row of detent members extending outwardly from said elongated member in the path of movement of said actuating wire arm and handle means mounted at the free end of said elongated member for pivotal movement of said elongated member out of said path of movement of said actuating wire arm.

* * * * *